United States Patent [19]

Becker et al.

[11] Patent Number: 4,692,406
[45] Date of Patent: Sep. 8, 1987

[54] PROCESS AND A REAGENT FOR THE SIMULTANEOUS DETERMINATION OF FIBRINOGEN AND FIBRINOGEN FISSION PRODUCTS IN PLASMA

[75] Inventors: Udo Becker, Marburg; Peter Roeschlau, Seeshaupt, both of Fed. Rep. of Germany

[73] Assignee: Boehringer Mannheim GmbH, Mannheim-Waldhof, Fed. Rep. of Germany

[21] Appl. No.: 642,421

[22] Filed: Aug. 20, 1984

[30] Foreign Application Priority Data

Aug. 25, 1983 [DE] Fed. Rep. of Germany ....... 3330699

[51] Int. Cl.$^4$ .............................................. C12Q 1/56
[52] U.S. Cl. ......................................... 435/13; 435/4; 435/23; 435/810; 436/69
[58] Field of Search ...................... 435/13, 4, 810, 214, 435/23; 436/69

[56] References Cited

U.S. PATENT DOCUMENTS 4,245,039 1/1981 Heimburger et al. ................ 435/13
4,289,498 9/1981 Baughman et al. .................... 436/34

OTHER PUBLICATIONS

Wenzel et al, Deutsche Medizinsches Wochenschrift 99(1974), 746-56, (translation included).
Becker et al., Abstract 96(1):3311v.
Wenzel et al., Abstract only, Deutsche Medizinsches Wochenschrift, Apr. 12, 1974, 99(15), pp. 746-756.
Bergmeyer, Methods of Enzymatic Analysis, 3rd edition, vol. V, Verlag Chemie GmbH, D-6940 Weinheim, 1984, pp. 493-499.
Siefring et al., Clin Chem., 29/4, 614-617 (1983).
Exner et al., Am. J. Clin. Pathol., 71, 521-527 (1979).
Becker et al., Throm Res., 35; 475-484 (1984).
Marguerie et al., Biochim Biophy Acta., 579 (1979), 134-141.

Primary Examiner—Christine M. Nucker
Attorney, Agent, or Firm—Felfe & Lynch

[57] ABSTRACT

The present invention provides a process for the simultaneous determination of fibrinogen and fibrinogen fission products in plasma, wherein 0.01 to 1 U of a snake venom enzyme with a thrombin-like effectiveness is aded per ml. of sample plasma, then there is measured the period of time between the addition of the enzyme and the commencement of a turbidity formation as a measure for the amount of fibrinogen fission products and subsequently there is measured the speed of the turbidity formation as a measure of the amount of fibrinogen.

The present invention also provides a reagent for the simultaneous determination of fibrinogen and fibrinogen fission products, wherein it comprises 0.01 to 10 U snake venon enzyme with thrombin-like effectiveness per ml. of sample plasma, 0.5 to 4% by weight of a water-soluble polyalcohol, 1 to 20 mMole/liter of calcium ions and 0.05 to 0.3 mole/liter of buffer of pH 7.0 to 8.0, referred to the solution ready for use, as well as optionally a detergent.

12 Claims, No Drawings

PROCESS AND A REAGENT FOR THE SIMULTANEOUS DETERMINATION OF FIBRINOGEN AND FIBRINOGEN FISSION PRODUCTS IN PLASMA

The present invention is concerned with a process and a reagent for the simultaneous determination of fibrinogen and fibrinogen fission products in plasma.

The determination of fibrinogen and of fibrinogen fission products (FFP) in plasma is important for the investigation of coagulation disturbances. A method which would permit the simultaneous determination of both parameters has hitherto not been known. The two parameters must be determined independently since the effects are superimposed.

For the determination of fibrinogen there are known not only immunological methods but also coagulation tests. The immunological methods are non-specific and do not permit a differentiation between fibrinogen and FFP. Furthermore, they display diagnostically serious disadvantages and have, therefore, not achieved any practical importance.

In the case of the coagulation tests, the fibrinogen content is determined by the time measurement of the coagulum formation. The greatest importance has been achieved by the method of Clauss (see Acta haemat., 17, 237–246/1957). In the case of this process, a diluted plasma, i.e. a weak fibrinogen solution, is mixed with a concentrated thrombin solution, the amount of thrombin thereby being about 500U/ml. of plasma. With the help of a calibration curve, the time up to the appearance of a coagulum is related to the fibrinogen content of the sample.

Furthermore, coagulation tests are known in which the turbidity formation in the course of coagulation is recorded photometrically, i.e. neither as an end point method nor as a kinetic method.

Finally, methods are also known in which the coagulum formed is isolated and the protein content thereof is determined. The sample is hereby reacted with thrombin and the coagulum formed is isolated, washed and dried and the protein content or the weight is then determined.

Methods for the determination of the FFP depend upon the coagulation-inhibiting action thereof.

The immunological determination with antibodies against fibrinogen or FFP is known. However, since no antibodies are known which only react with FFP but not with fibrinogen and, on the other hand, since antibodies against fibrinogen also always react with FFP, this determination requires a previous separation of fibrinogen and FFP.

In addition, the coagulation-inhibiting action of FFP is also used directly for the determination. In this case, the sample is reacted with thrombin and the time up to the commencement of coagulation is measured since FFP exerts a thrombin-inhibiting effectiveness.

From the above, it follows that, in principle, admittedly the same technique is employed not only for the fibrinogen determination but also for the FFP determination, namely, the reaction of plasma with thrombin and the determination of the time up to the commencement of coagulation. However, there is a fundamental difference in the choice of the enzyme concentration with regard to the sample used. Clauss was the first to appreciate that the coagulation time of a plasma sample reacted with thrombin is proportional to the fibrinogen content when there is selected a sufficiently great ratio of thrombin to the amount of sample, in the particular case 500U/ml. of plasma. The main disturbing factors are hereby antithrombins, i.e. those substances which inhibit the action of thrombin, antithrombin III, antithrombin BM and $\alpha_2$-macroglobulin, as well as FFP, being known.

Therefore, in the case of all known methods for the determination of fibrinogen, the attempt is made to keep small the influence of the mentioned disturbing factors, at least by a corresponding increase of the amount of enzyme. It is also known to reduce the influence of the disturbing factors, which is increased in the presence of small amounts of haparin, by means of heparin antagonists.

If, on the other hand, FFP is determined, then the thrombin concentration is kept very low since otherwise the fibrinogen concentration strongly influences the result. However, under these conditions, the influence of the plasmatic inhibitors increases so that this method is not especially specific.

From J. Lab. Clin. Meth., 58, 477/1961, there is also known a turbidimetric fibrinogen determination. This is an end point process with the use of a standard which, as a result of the long incubation time of 20 minutes, does not permit an automation thereof. The process described in Clin. Chem., 29, 614/1983 overcomes this disadvantage by kinetic measurement with a time interval of about 17 seconds. However, in this case, a minimum activity of 12 NIH U thrombin/ml. of plasma is required and a non-linear calibration relationship is obtained between the measurement signal and the amount of fibrinogen, which can only be evaluated laboriously. Therefore, this process is not suitable for a routine test.

Therefore, it is an object of the present invention to provide a process which avoids the above-described disadvantages, requires an especially short measurement time with low enzyme activities and permits the simultaneous determination not only of fibrinogen but also of FFP.

Thus, according to the present invention, there is provided a process for the simultaneous determination of fibrinogen and of fibrinogen fission products in plasma, wherein 0.01 to 1U of a snake venom enzyme with a thrombin-like effectiveness is added per ml. of plasma, then there is determined the period of time between the addition of the enzyme and the commencement of a turbidity formation as a measure for the amount of fibrinogen fission products and subsequently there is measured the speed of turbidity formation as a measure of the amount of fibrinogen.

The present invention is based upon the recognition that, in the case of the replacement of thrombin by a snake venom enzyme in the stated low activity, the known disturbing factors are practically excluded and not only the period of time between the addition of the snake venom enzyme and the commencement of the formation of turbidity but also the speed of the turbidity formation itself are, in each case, directly proportional to the amount of FFP or fibrinogen. In the case of the present invention, the best results are achieved with an enzyme concentration of from 0.05 to 0.5U.

The snake venom enzymes used are those with a thrombin-like effectiveness. Preferably, there is used batroxobin, the venom enzyme of the Malayan pit viper (*Aqkistrodon rhodostoma*) and the venom enzyme of the copperhead snake (*Agkistrodon contortix*).

In a preferred embodiment of the process according to the present invention, it is carried out in the presence of 0.5 to 4% by weight of a water-soluble polyalcohol, the polyalcohol increasing the uniformity of the turbidity formation. Examples of polyalcohols which can be used include starch, dextran, polyvinyl alcohol, polyethylene glycol, sugars and sugar polymers. Especially good results have been obtained with a polyethylene glycol with a molecular weight of from 4000 to 22,000.

The process according to the present invention is carried out at a pH value of from 7.0 to 9.0 and preferably at a pH value of from 7.3 to 7.8. However, all that is important is that the pH value lies in the physiological range. The buffer concentration is preferably from 0.05 to 0.3 mole/liter of buffer solution. All buffer substances buffering in the given range which are physiologically compatible can be used according to the present invention. As examples, there may be mentioned tris/HCl and phosphate buffers.

Furthermore, in known manner, the process is carried out in the presence of a soluble calcium salt which provides calcium ions in an amount of from 1 to 20 mMole/liter. Examples of appropriate calcium salts include calcium halides, such as calcium chloride, as well as calcium acetate and the like.

Finally, the addition of a detergent, for example Brij 35, has also proved to be expedient. Appropriate amounts are in the range of from 0.1 to 2%.

The present invention also provides a reagent for carrying out the above-described process, which comprises 0.01 to 1U snake venom enzyme with a thrombin-like effectiveness per ml. of plasma sample, 0.5 to 4% by weight of a water-soluble polyalcohol, 1 to 20 mMole/liter of calcium ions and 0.05 to 0.3 mole/liter of buffer of pH 7.0 to 9.0, in each case referred to the solution ready for use, as well as optionally a detergent.

The reagent according to the present invention can be present as a mixture of the dry substances or also in the form of a concentrated or ready-for-use dilute solution.

By means of the present invention, it is achieved that, in an analysis with a very small time requirement and a single calibration, there can be simultaneously determined not only fibrinogen but also FFP, disturbances due to antithrombins thereby being excluded. At the same time, only minimum amounts of enzyme are required.

The following Examples are given for the purpose of illustrating the present invention:

EXAMPLE 1

The following solutions are prepared:
Solution 1:
10U Batroxobin are dissolved in 1 ml. of water.
Solution 2:
A solution is prepared which contains 0.1 mole/liter tris/HCl (pH 7.5), 5 mMole/liter calcium chloride, as well as 1% Brij 35 and 2% polyethylene glycol 6000.
Solution 3:
(reaction mixture) 90 µl. of Solution 1 are mixed with 100 ml. of Solution 2.

A photometric measurement is carried out under the following conditions:
photometer with recorder, wavelength 340 nm, semi-microcuvette with a layer thickness of 1 cm., temperature 25° C., recorder speed 1 cm./minute.

0.1 ml. of a fibrinogen-containing sample is taken and the reaction is initiated by the addition of 1.0 ml. of the reaction mixture which has been warmed to 25° C., the recorder being started simultaneously. From the linear part of the resulting recorded diagram there is read off the change of extinction per unit time. The process is repeated with a solution of known fibrinogen content. From the extinction changes read off, there can be calculated the concentrations of the unknown sample.

EXAMPLE 2

30 Citrate plasma samples, such as are obtained routinely in a hospital, are analysed according to the method described in Example 1. The same plasma samples are also analysed according to a conventional coagulation-physiological routine method (Clauss test). The method comparison gives a correlation coefficient of $r = 0.95$.

EXAMPLE 3

Human citrate plasma with a fibrinogen content of about 400 mg./dl. is warmed to 37° C. and mixed with streptokinase (100U/ml.). At definite times, aliquots of aprotonin (3000 KI/ml.) are added and the finding rate for fibrinogen determined with two known methods as well as with the method according to the present invention. The results obtained are set out in the following Table 1. The amount of fibrinogen actually present in the samples is determined by the Ratnoff-Menzie method (see column 2), which is generally regarded as being a reference method not subject to disturbances. The other two methods show, with an increasing portion of fission products, a reduced finding rate; however, the process according to the present invention gives clearly better results than the routine method according to Clauss.

TABLE 1

| Finding rate for fibrinogen in plasma samples which have been treated with streptokinase; reference method according to Ratnoff-Menzie; average of three experiments | | | |
| --- | --- | --- | --- |
| breakdown time (min.) | reference method % | kinetic turbidity test according to the invention % | Clauss test % |
| 0 | 100 | 100 | 100 |
| 2 | 95.7 | 95.1 | 94.9 |
| 5 | 91.0 | 88.0 | 78.9 |
| 10 | 83.5 | 67.4 | 53.3 |
| 20 | 61.5 | 41.5 | 30.2 |
| 40 | 46.5 | 28.8 | 19.0 |
| 60 | 41.2 | 24.3 | 12.8 |

EXAMPLE 4

Citrate plasma is subjected to a fibrinolytic breakdown according to Example 3, aliquots again being taken at appropriate times and stopped with aprotonin. The content of fission products in the samples is given by the difference from the original fibrinogen content and the fibrinogen content of the samples (determined by the Ratnoff-Menzie method). On the samples, there is again determined, by means of the process according to the present invention, the time which passes after the start of the reaction up to the commencement of a change in the turbidity. When the fission product content of the samples is plotted against these measurement values, then there is obtained a linear relationship (see the following Table 2) with a correlation coefficient of $r = 0.99$; i.e. the investigated parameter is a measure for the concentration of the fission products present in the sample.

TABLE 2

Relationship between FFP concentration and lag phase in the kinetic turbidity test according to the present invention

| breakdown time (min.) | FFP mg./dl. | reaction time (lag phase) (sec.) |
| --- | --- | --- |
| 0 | 0 | 7.2 |
| 2 | 20.0 | 13.5 |
| 5 | 19.0 | 26.4 |
| 10 | 25.6 | 36.9 |
| 15 | 38.0 | 85.2 |
| 20 | 61.3 | 125 |
| 40 | 114 | 242 |
| 60 | 140 | 318 |
| 120 | 192 | 425 |

We claim:

1. A process for the simultaneous determination of fibrinogen and fibrinogen fission products in plasma, comprising adding 0.01 to 1U of a snake venom enzyme with thrombin-like activity per ml. of sample plasma, measuring the period of time between the addition of the enzyme and the commencement of a turbidity formation as a measure of the amount of fibrinogen fission products, and subsequently measuring the speed of the turbidity formation as a measure of the amount of fibrinogen.

2. The process of claim 1, wherein said enzyme is snake venom enzyme batroxobin, the venom enzyme of the Malayan pit viper (*Aqkistrodon rhodostoma*) or the venom enzyme of the copperhead snake (*Agkistrodon contortix*)

3. The process of claim 1, wherein 0.5 to 4% by weight of a water-soluble polyalcohol is added.

4. The process of claim 3, wherein the polyalcohol used is starch, dextran, polyvinyl alcohol, polyethylene glycol, a sugar or a sugar polymer.

5. The process of claim 4, wherein the polyethylene glycol has a molecular weight of from 4,000 to 22,000.

6. The process of claim 1 wherein the determination is carried out at a pH value of from 7.0 to 9.0.

7. The process of claim 1 wherein the determination is carried out in a 0.05 to 0.3 mole/liter buffer solution.

8. The process of claim 1 wherein calcium ions are added in an amount of from 1 to 20 mMole/liter.

9. A reagent for the simultaneous determination of fibrinogen and fibrinogen fission products, comprising 0.01 to 1.0U snake venom enzyme with thrombin-like activity per ml. of sample plasma, 0.5 to 4% by weight of a water-soluble polyalcohol, 1 to 20 mMole/liter of calcium ions and 0.05 to 0.3 mole/liter of buffer of pH 7.0 to 8.0, referred to the solution ready for use.

10. The reagent of claim 9 further comprising a detergent.

11. The reagent of claim 9 wherein a tris/HCl or a phosphate buffer is used.

12. The process of claim 7 wherein a tris/HCl or a phosphate buffer is used.

* * * * *

UNITED STATES PATENT AND TRADEMARK OFFICE
CERTIFICATE OF CORRECTION

PATENT NO. : 4,692,406

DATED : September 8, 1987

INVENTOR(S) : Udo Becker, et al.

It is certified that error appears in the above-identified patent and that said Letters Patent is hereby corrected as shown below:

Claim 1, line 4: delete "with thrombin-like activity" and replace with -- which hydrolyzes fibrinogen to produce fibrin --.

Claim 9, lines 3 and 4: delete "with thrombin-like activity" and replace with -- which hydrolyzes fibrinogen to produce fibrin --.

Signed and Sealed this

Twenty-fourth Day of May, 1988

Attest:

DONALD J. QUIGG

Attesting Officer

Commissioner of Patents and Trademarks